(12) United States Patent
Mirza et al.

(10) Patent No.: US 11,172,973 B2
(45) Date of Patent: Nov. 16, 2021

(54) INTRAMEDULLARY PIN, CLAMP AND METHOD OF USE THEREOF

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. Surgical, Inc., Smithtown, NY (US)

( * ) Notice: Subject to any disclaimer, the term of this patent is extended or adjusted under 35 U.S.C. 154(b) by 0 days.

(21) Appl. No.: 16/264,748

(22) Filed: Feb. 1, 2019

(65) Prior Publication Data

US 2019/0159814 A1    May 30, 2019

Related U.S. Application Data

(63) Continuation of application No. 15/694,233, filed on Sep. 1, 2017, now Pat. No. 10,687,872.

(51) Int. Cl.
*A61B 17/92* (2006.01)
*A61B 17/72* (2006.01)
(Continued)

(52) U.S. Cl.
CPC ............ *A61B 17/921* (2013.01); *A61B 17/72* (2013.01); *A61B 17/7283* (2013.01);
(Continued)

(58) Field of Classification Search
CPC .... A61B 17/8872; A61B 17/921; A61B 17/92
See application file for complete search history.

(56) References Cited

U.S. PATENT DOCUMENTS

| 4,862,883 A | 9/1989 | Freeland |
| 5,499,986 A | 3/1996 | Dimarco |

(Continued)

FOREIGN PATENT DOCUMENTS

| FR | 2668919 | 5/1992 |
| FR | 2668919 A1 * | 5/1992 ........... A61B 17/921 |

OTHER PUBLICATIONS

File History of U.S. Appl. No. 15/694,233, filed Sep. 1, 2017.

*Primary Examiner* — Julianna N Harvey
(74) *Attorney, Agent, or Firm* — Bodner & O'Rourke, LLP; Gerald T. Bodner; Christian P. Bodner

(57) ABSTRACT

An intramedullary pin includes a main body having a proximal boundary and a distal boundary; a curved extension having a degree of curvature of at least 1°, the curved extension being in direct contact with the distal boundary; a distal cap having a cylindrical portion and a rounded portion, the cylindrical portion being in direct contact with the curved extension; a grip element having at least one contour, the grip element being in direct contact with the proximal boundary; and a proximal cap having a flat surface, the proximal cap being in direct contact with the grip element. Also disclosed is a clamp that includes a handle, two blades, a pivot, and a plurality of grasping elements including a notch, at least one protrusion, and a groove, where one or more grasping elements have a contour that is structurally complementary to the grip element in the intramedullary pin. A method of immobilizing a bone fracture using the intramedullary pin and/or clamp is also disclosed.

8 Claims, 8 Drawing Sheets

(51) Int. Cl.
  *A61B 17/88* (2006.01)
  *A61B 17/56* (2006.01)
  *A61B 17/00* (2006.01)
  *A61B 17/062* (2006.01)

(52) U.S. Cl.
  CPC ...... *A61B 17/7291* (2013.01); *A61B 17/8872* (2013.01); *A61B 17/062* (2013.01); *A61B 2017/00738* (2013.01); *A61B 2017/564* (2013.01)

(56) References Cited

U.S. PATENT DOCUMENTS

| | | | |
|---|---|---|---|
| 5,562,447 | A | 10/1996 | Moy et al. |
| 6,136,004 | A | 10/2000 | Keller |
| 6,143,012 | A | 11/2000 | Gausepohl |
| 2003/0216738 | A1* | 11/2003 | Azar ................. A61B 17/7208 606/326 |
| 2006/0200142 | A1* | 9/2006 | Sohngen ................ A61B 17/72 606/62 |
| 2007/0173834 | A1 | 7/2007 | Thakkar |
| 2008/0147067 | A1 | 6/2008 | Phillips |

\* cited by examiner

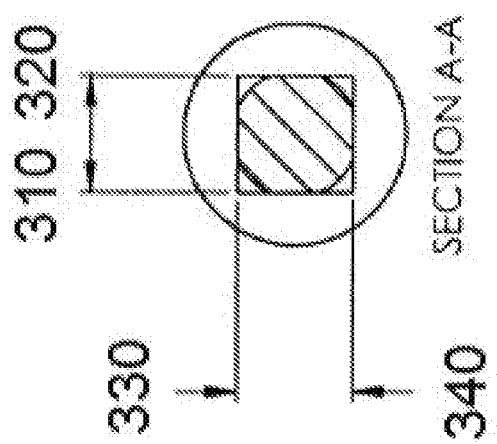

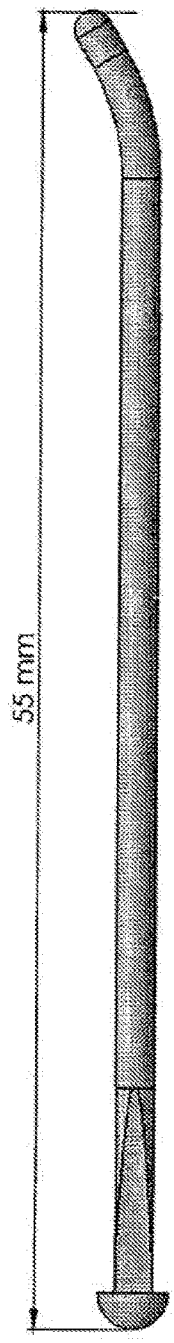
FIG. 4  55 mm
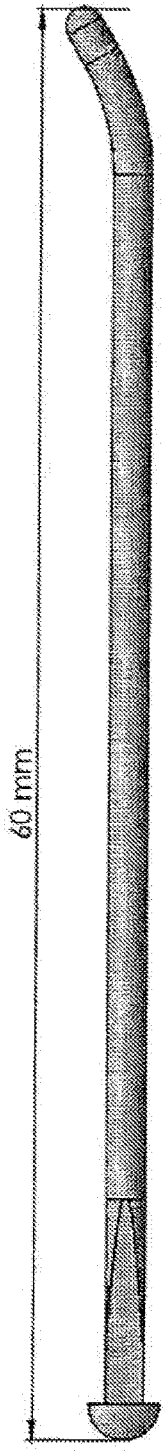
FIG. 5  60 mm
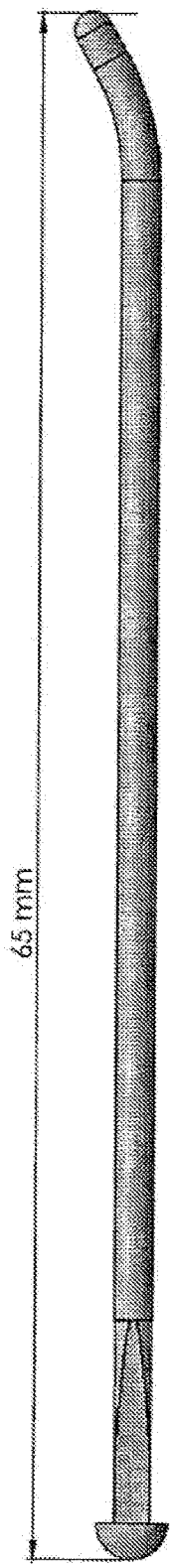
FIG. 6  65 mm
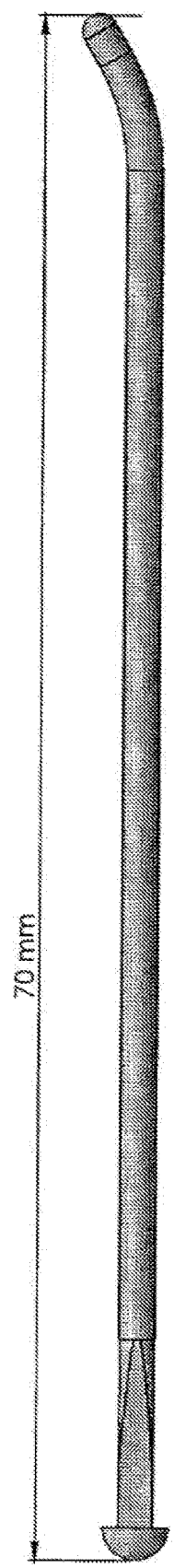
FIG. 7  70 mm
FIG. 8

900

SECTION A-A

SECTION B-B

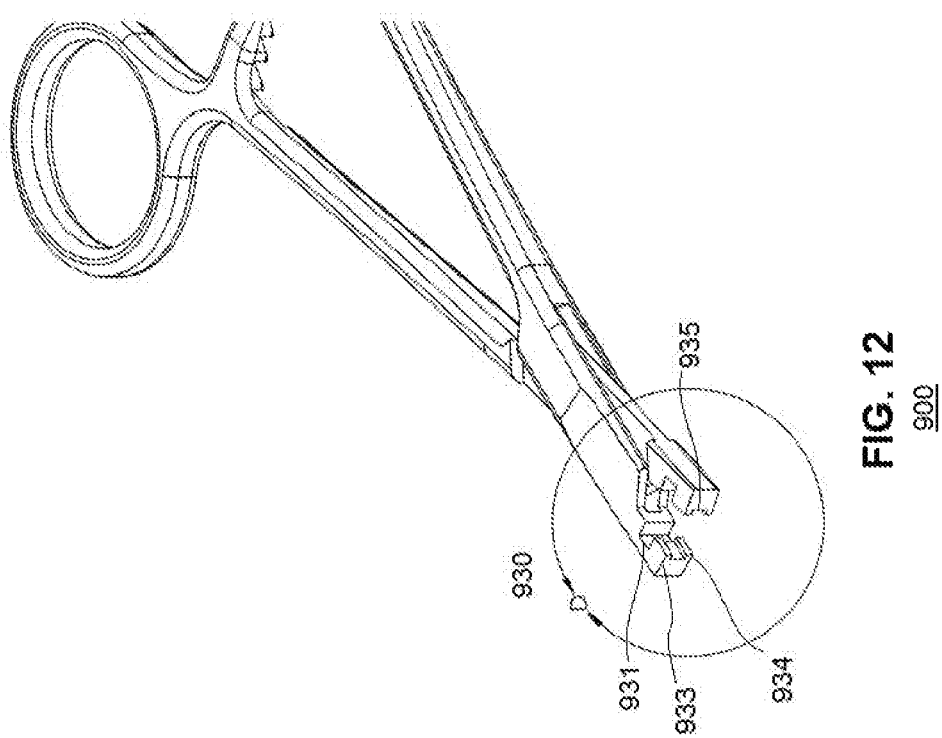

930

930

INTRAMEDULLARY PIN, CLAMP AND METHOD OF USE THEREOF

This application is a Continuation of U.S. application Ser. No. 15/694,233, filed Sep. 1, 2017. The entirety of the aforementioned applications is incorporated herein by reference.

FIELD

The present application relates generally to medical devices and more specifically, to an intramedullary pin, a clamp and methods of using the same.

BACKGROUND

A bone fracture may be caused by single impact or torque, an accumulation of small stresses due to fatigue, overuse, repetitive activities, or medical conditions that weaken bones, such as bone cancer or osteoporosis. There are hundreds of thousands, if not millions, of bone fractures each year in the United States, and many more instances of bone fractures world-wide.

Bone fractures are generally treated by immobilization, where the fractured bone is reset into place and immobilized. Common approaches to immobilization include applying casts made of plaster or other material and/or placing the patient in traction. Additional methods of treatments include bone grafting and implantation.

When these treatment methods are employed, the patient is forced into a significant period of partial, or complete, inactivity, depending upon the nature and severity of the fracture. If a cast is used for immobilization, it will often be necessary to immobilize a large area of the body surrounding the fracture. While healing occurs, the muscles surrounding the fracture may atrophy from lack of movement and use, which adds to recovery time.

Bone grafting and implantation require one or more invasive surgical procedures, in which the patient undergoes local or general anesthesia. As with any surgical procedure, there is an increased risk of infection and the patient will also experience some discomfort during recovery. Rehabilitation will also be necessary, resulting in the patient spending additional time away from work or other activities.

Another concern when treating bone fractures is proper healing. In order to achieve optimal healing and recovery, the bone fragments should be completely reset and placed in the same alignment present before the fracture occurred. Depending upon the bone involved and the type of fracture, this may be difficult to achieve. In particular, it may be difficult to reset spiral fractures, compression fractures, and displaced fractures; further difficulty may be encountered in maintaining the bone fragments in proper position during healing and rehabilitation.

Thus, there is a need for a device that can be inserted into the medullary cavity of a fractured bone, and if necessary, to be removed in a manner that minimizes surgical invasion and the risk of further injury to the patient. There also exists a need for a device to adequately fill the medullary cavity and hold the bone fragments in proper alignment during healing and rehabilitation, and consequently there is a need to precisely position the device within the medullary cavity.

SUMMARY

One aspect of the present application is an intramedullary pin for immobilizing a fractured bone. The intramedullary pin comprises a main body; a curved extension having a radius of curvature; a distal cap having a cylindrical portion and a rounded portion; a grip element having at least one contour; and a proximal cap having a flat surface, where the degree of curvature is between 1° to 45°.

In some embodiments, a distal boundary of the main body is in direct contact with the curved extension, the curved extension is in direct contact with the cylindrical portion of the distal cap, a proximal boundary of the main body is in direct contact with the grip element, and the grip element is in direct contact with the flat surface of the proximal cap.

In other embodiments, the at least one contour of the grip element comprises at least one of an angled surface, depression, hatching, indentation, protuberance, ridge, slot, rail, track, hook, loop, alternating smooth and coarse section, or a combination thereof.

In other embodiments, the at least one contour of the grip element is structurally complementary to at least one contour on a grasping element of a clamp.

In other embodiments, the proximal cap has a hemispherical shape that fits into a notch in a clamp.

In other embodiments, the main body, the curved extension, the distal cap, the grip element, and the proximal cap are composed of at least one of stainless steel, titanium, nitinol and a bioabsorbable material.

In some embodiments, the curved extension has a degree of curvature in the range of about 5° to 45°, 10° to 40°, 15° to 35°, 20° to 30° or 25° to 35°. In some embodiments, the curved extension has a degree of curvature of about 25° or about 30°.

In some embodiments, the fractured bone is a long bone.

Another aspect of the present application is a clamp, comprising: a handle; two blades; a pivot; and one or more grasping elements including a notch, at least one protrusion, and a groove, where at least one of the grasping elements has at least one contour.

In other embodiments, the at least one contour on the at least one grasping elements comprises at least one of an angled surface, depression, hatching, indentation, protuberance, ridge, slot, rail, track, hook, loop, alternating smooth and course section, or a combination thereof.

In other embodiments, the at least one contour on the at least one grasping element is structurally complementary to the contour on a grip element of an intramedullary pin.

In other embodiments, the notch of the clamp has an inverse hemispherical shape that fits into a proximal cap of an intramedullary pin.

In other embodiments, the handle, blades, pivot, and grasping elements are composed of at least one of stainless steel, titanium and nitinol.

Another aspect of the present application relates to an instrument kit. In some embodiments, the kit includes an intramedullary pin which comprises: a main body having a proximal boundary and a distal boundary; a curved extension having a radius of curvature, where the curved extension is in direct contact with the distal boundary; a distal cap having a cylindrical portion and a rounded portion, where the cylindrical portion is in direct contact with the curved extension; a grip element having at least one contour, where the grip element is in direct contact with the proximal boundary; and a proximal cap having a flat surface, where the proximal cap is in direct contact with the grip element.

In some embodiments, the kit includes a clamp comprising: a handle; two blades; a pivot; and one or more grasping elements including a notch, at least one protrusion, and a groove, where at least one of the grasping elements has at least one contour. In some embodiments, the at least one contour on the at least one grasping elements comprises at least one of an angled surface, depression, hatching, indentation, protuberance, ridge, slot, rail, track, hook, loop, alternating smooth and course section, or a combination thereof. In other embodiments, the at least one contour on the at least one grasping element is structurally complementary to the contour on a grip element of an intramedullary pin.

In some embodiments, the instrument kit is a kit for immobilizing a fractured bone includes an intramedullary pin and a complementary clamp. The intramedullary pin comprises: a main body having a proximal boundary and a distal boundary; a curved extension having a radius of curvature, where the curved extension is in direct contact with the distal boundary; a distal cap having a cylindrical portion and a rounded portion, where the cylindrical portion is in direct contact with the curved extension; a grip element having at least one contour, where the grip element is in direct contact with the proximal boundary; and a proximal cap having a flat surface, where the proximal cap is in direct contact with the grip element. The clamp of the instrument kit comprises a handle; two blades; a pivot; and grasping elements including a notch, at least one protrusion, and a groove, where at least one of the grasping elements has at least one contour. In some embodiments, the at least one contour of the grip element comprises at least one of an angled surface, groove, hatching, indentation, protrusion, ridge, slot, rail, track, hook, loop, alternating smooth and coarse section, or a combination thereof. In some embodiments, the at least one contour on the at least one grasping element of the clamp is structurally complementary to the contour on the grip element of the intramedullary pin. In other embodiments, the notch of the clamp has an inverse hemispherical shape that is structurally complementary to the proximal cap of the intramedullary pin.

Another aspect of the present application relates to a method of reducing movement of, or immobilizing, a bone fracture in a subject using the intramedullary pin comprising: establishing an access point to the medullary cavity of the bone; reducing the bone fragments at the fracture; aligning the intramedullary pin at the access point; inserting the intramedullary pin at replace access point and into the intramedullary cavity; and positioning the intramedullary pin within the intramedullary cavity, thereby reducing movement of, or immobilizing, the bone fragments in the reduced state. In some embodiments, the method further comprises the step of grasping a grip element and a proximal cap the intramedullary pin with a grasping device.

In some embodiments, the bone is a long bone. In other embodiments, the subject is a mammal. In other embodiment, the subject is a human.

Another aspect of the present application relates to a method of reducing movement of, or immobilizing, a bone fracture using the intramedullary pin and the clamp of the present application, comprising: establishing an access point to the medullary cavity of the bone; reducing the bone fragments at the fracture; grasping a grip element and a proximal cap the intramedullary pin with one or more grasping elements of the clamp; aligning the intramedullary pin at the access point; inserting the intramedullary pin at replace access point and into the intramedullary cavity; and positioning the intramedullary pin within the intramedullary cavity, thereby reducing movement of, or immobilizing, the bone fragments in the reduced state.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIG. 3 is a height-wise cross-sectional view of the intramedullary pin embodiment depicted in FIG. 1.

FIG. 4 is a perspective view of an embodiment of an intramedullary pin of the present application.

FIG. 5 is a perspective view of an embodiment of an intramedullary pin of the present application.

FIG. 6 is a perspective view of an embodiment of an intramedullary pin of the present application.

FIG. 7 is a perspective view of an embodiment of an intramedullary pin of the present application.

FIG. 8 is a perspective view of an embodiment of an intramedullary pin of the present application.

FIG. 12 is a perspective view of the clamp embodiment depicted in FIG. 9.

DETAILED DESCRIPTION

Figure 1:
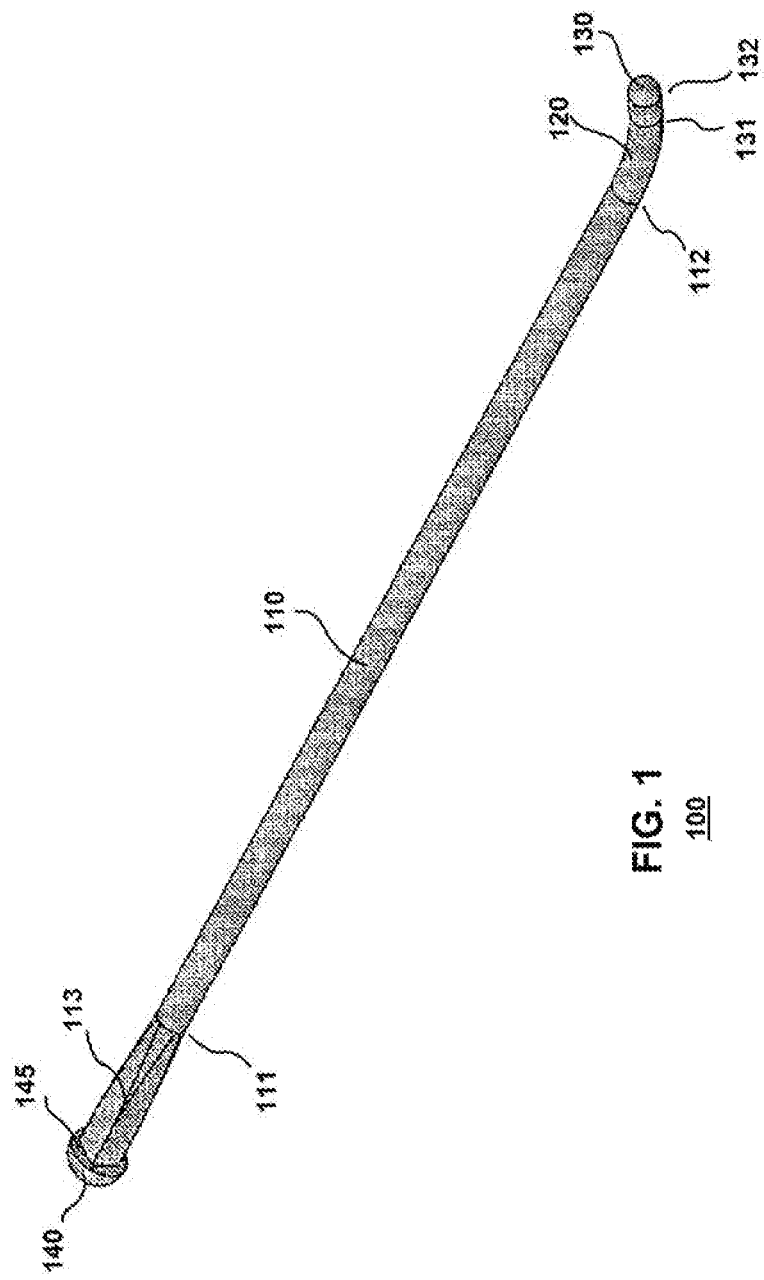
FIG. 1 is a perspective view of an embodiment of an intramedullary pin of the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily drawn to scale and certain features of the application may be shown exaggerated in scale or in somewhat schematic form in the interest of clarity and conciseness. In the description, relative terms such as "front," "back," "up," "down," "top," "bottom," "upper," and "lower," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship where structures are secured or attached to one another either directly or indirectly through intervening structures, as well as both movable or rigid attachments or relationships, unless expressly described otherwise.

As used herein, the terms "horizontal" and "vertical," and derivatives of those terms, are used in respect to their relationship to the plane defined by the lengthwise body of the Intramedullary pin of the present invention. "Horizontal" refers to the plane that can, for example, pass through the lengthwise body of the Intramedullary pin, while "vertical" refers to a plane that is perpendicular to the horizontal plane.

The term "bone," as used herein, refers to any part of the vertebrate skeleton of a mammal, such as a human, including long bones, short bones, flat bones, irregular bones, and sesamoid bones.

The term "long bone," as used herein, refers a bone having a greater length than width and having a shaft and two extremities. Long bones are found in the limbs and include the clavicle, humerus, radius, ulna, femur, tibia, fibula and the metacarpal and metatarsal bones, including the phalanges.

The terms "fracture" or "bone fracture," as used herein, refer to any damage to the continuity of a bone, including damage caused by impact, torque, fatigue, overuse, or repetitive activities, or bone-weakening medical conditions.

The terms "reduction," "reduced," and "reducing," as used herein, refer to a medical procedure to restore a fracture to the correct alignment by moving the fragments into contact with one another in the correct position for bone healing.

The term "fixation element," as used herein, refers to an element that completely or partially embeds into bone, bone fragments, or hard tissue to fasten in order to immobilize reduced bone fragments so that the fragments can grow together. Examples of fixation elements include, but are not limited to, intramedullary pins, nails, staples, rods, wires and screws. Fixation elements of the present invention can be composed of any suitable biocompatible material including, but not limited to, metal alloys, polymers, bioabsorbable materials, ceramic, or combinations thereof.

The term "proximal" end of a device, or a part of a device, as used herein, is the end that is towards the practitioner holding or operating the device. The "distal" end of a device, or a part of a device, as used herein, is the end that is towards the subject into whom the device, or part of the device, is to be delivered. In some embodiments, the proximal end and distal end are referred to as the trailing end and leading end, respectively.

The term "structurally complementary," as used herein, refers to a first structural element having a shape adapted to fit with a second element to form a composite structural combination, such as a lock and key, etc.

The term "subject" as used herein includes, without limitation, a human, mouse, rat, guinea pig, dog, cat, horse, cow, pig, monkey, chimpanzee, baboon, or rhesus. In some embodiments, the subject is a mammal. In some embodiments, the subject is a human. In some embodiments, the subject is a pet or an animal.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

The term "pet" or "animal" may include any generally non-human animal which is owned or otherwise cared for, at least in part, by a human for the purposes of amusement, entertainment, husbandry, rehabilitation, companionship or the like, wherein several examples of these types of pets may include mammals, birds, reptiles, amphibians, fish, and invertebrates, and may specifically include but are not limited to dogs, cats, hamsters, cattle, horses, or a combination thereof. Additionally, it is contemplated that the teachings of embodiments of the present invention may also be adapted for use with many types of wild or exotic animals that are held in captivity such as may be found in a typical zoo.

Pin

One aspect of the present application relates to a rod-shaped pin. In some embodiments, the pin is an intramedullary pin that may be used as a fixation element for insertion into, and immobilization of, fragments of a fractured bone in a body of a subject. In a particular embodiment, the subject is a human. In another embodiment, the subject is an animal. In another embodiment, the subject is a mammal. In another embodiment, the subject is a pet.

The intramedullary pin of the present application may be employed with fragments of any fractured bone. In a particular embodiment, the fractured bone is a long bone. In other particular embodiments, the intramedullary pin of the present application can be used to immobilize the fragments of a fractured short bone, including the patella, sesamoid, carpal and tarsal bones. In further particular embodiments, the intramedullary pin of the present application can be used to immobilize the fragments of a fractured flat bone, including the skull, cranium, occipital, parietal, frontal, nasal, lachrymal, vomer, scapula, os innominatum, sternum, and rib bones. In additional particular embodiments, the intramedullary pin of the present application can be used to immobilize the fragments of a fractured irregular bone, including the vertebrae, sacrum, coccyx, temporal, sphenoid, ethmoid, malar, superior maxillary, inferior maxillary, palate, inferior turbinated, and hyoid bones.

The intramedullary pin of the present application includes a substantially horizontal main body having a curved extension with a degree of curvature for use in immobilizing bone fragments of a reduced fracture. The curved extension may allow for a less disruptive insertion into the intramedullary cavity, and once inserted, may further allow for greater stability in immobilizing the bone fracture, particularly with respect to rotational stability. In some embodiments, the degree of curvature is greater than 1°. In some embodiments, the curved extension has a degree of curvature in the range of about 1° to 45°, 5° to 45°, 10° to 40°, 15° to 35°, 20° to 30° or 25° to 35°. In some embodiments, the curved extension has a degree of curvature of about 25° or about 30°.

The intramedullary pin of the present application may further include a grip element to facilitate grasping by a clamp. The grip element may have one or more contoured surfaces, such as angled planes, grooves, indentations and protrusions. These contoured surfaces are configured for fitting into contoured surfaces present on the grasping elements of a clamp by, for example, placing inversions of the grip element contours on the grasping elements of the clamp. In addition, the intramedullary pin may include a proximal cap in a hemispherical shape, for example, and the clamp may be correspondingly provided with an inverse hemispherical notch. By employing complementary grip and grasping elements, the clamp and intramedullary pin may offer a medical practitioner an improved grasp of, and consequently greater control over the intramedullary pin during insertion into and placement within the intramedullary cavity, as well as during extraction of the intramedullary pin, should the need arise.

FIG. 1 shows an exemplary intramedullary pin 100 of the present application. In this embodiment, the intramedullary pin 100 comprises a main body 110, a curved extension 120, and distal cap 130. The intramedullary pin 100 may further include a proximal cap 140.

The main body 110 may be an elongated element that constitutes the majority of the length of the intramedullary pin 100, and may define a main axis for the pin 100 in the horizontal direction. The main body 110 may include a proximal boundary 111 and distal boundary 112, and these boundaries may be located towards the proximal and distal ends of the Intramedullary pin 100, respectively. Between the proximal boundary 111 and the distal boundary 112, the main body 110 may have a substantially even surface, and may be without indentations or protrusions.

The intramedullary pin 100 may be inserted into the medullary cavity of a fractured bone in such a way that the main body 110 is aligned substantially parallel to the shape of the cavity. In this orientation, the main body 110 may immobilize the reduced bone fragments in the correct position to allow union of the fragments at the fracture. In addition to immobilizing the bone fragments, the main body 110 may provide internal support to the bone fragments, reducing the external stress and pressure borne by the bone and further facilitating healing and recovery.

The main body 110 further comprises a grip element 113, in direct contact with the proximal boundary 111. In some embodiments the grip element may be contoured or otherwise shaped in a manner to support clasping by the clamp 900, embodiments of which are described in further detail below. The contours of the grip element 113 may be structurally complementary to the shape of the grasping elements 930 of the clamp 900, such that the grasping element of the clamp may have contours that are the inverse of the contours of the grip element 113, for example. Accordingly, the clamp 900 may securely grasp the intramedullary pin 100 during insertion and placement of the pin in the medullary cavity. Similarly, this correspondence may further support the secure gasping and extraction of the intramedullary pin 100 in cases where the pin is to be removed from the medullary cavity. The grip element 113 fits securely into grasping slot 935 with room from 931 to accommodate proximal cap 140.

The grip element 113 may be contoured along its length in various ways, including but not limited to angled surfaces, grooves, hatching, indentations, protrusions, ridges, slots, rails, tracks, hooks, loops, alternating smooth and coarse sections, or any combination thereof. It is understood that the contours of the grip element 113 may be shaped in any manner in correspondence with the grasping elements 930 of the clamp 900 while still maintaining effective contact and support within the medullary cavity.

In some embodiments, the grip element 113 may be contoured to facilitate insertion into a cross-pin fixator, such as the cross-pin fixator described by U.S. Pat. No. 8,852,248 to Mirza et al., the contents of which are incorporated by reference herein in their entirety. The contours of the grip element 113 allow the intramedullary pin 100 to be securely grasped and fixed in place by the cross-pin fixator.

As shown in FIG. 1, located on the opposite end of the main body 110 from the proximal boundary 111 may be the distal boundary 112. The intramedullary pin 100 may further comprise a curved extension 120, in direct contact with the distal boundary 112. Unlike the main body 110, the curved extension 120 may not be substantially horizontal, and instead may be formed having a radius of curvature directed away from the main axis of the Intramedullary pin 100 as defined by the horizontal length of the main body 110.

The curved extension 120 may improve the insertion and placement of the intramedullary pin 100 into the intramedullary cavity. The curved extension 120 may allow for a smoother and less disruptive insertion into the cavity. Once the intramedullary pin 100 has been inserted, the curved extension 120 may improve the stability of the pin within the intramedullary cavity and may prevent movement of the intramedullary pin 100 within the cavity. In particular, the curved extension 120 may improve rotational stability of the intramedullary pin 100 within the intramedullary cavity. Each of these aspects may improve the immobilization of bone fragments and promote the proper union of fragments at the reduced fracture. Further, in cases where removal of the intramedullary pin 100 is necessary, the curved extension 120 may allow for the pin to be removed in a smoother and less disruptive manner.

In some embodiments, the intramedullary pin 100 further includes a distal cap 130, which may be in direct contact with the curved extension 120. The distal cap 130 may include two portions, a cylindrical portion bounded by the intermediate boundaries 131 and 132, and a rounded portion extending from intermediary boundary 132 to the end of the cap. Unlike the curved extension 120, the cylindrical portion of the distal cap 130 may lack a radius of curvature, and instead may be formed with as a right circular cylinder with a straight line axis.

The rounded portion of the distal cap 130 may form the distal end of the intramedullary pin 100. In some embodiments, the rounded portion may have a bowl or dome shape. In other embodiments the rounded portion may be hemispherical in shape, in other embodiments the rounded portion may be semispherical in shape, and in other embodiments the rounded portion may be in the shape of a geodesic dome.

Like the curved extension 120, the shape of the cylindrical portion and the rounded portion of the distal cap 130 may improve the insertion and placement of the intramedullary pin 100 into the intramedullary cavity, and may also allow for a less disruptive removal of the intramedullary pin 100, if necessary. Further, once inserted, the distal cap 130 may improve the stability of the intramedullary pin 100 within the intramedullary cavity.

The intramedullary pin 100 may further include a proximal cap 140 in direct contact with the grip element 113. In some embodiments, the proximal cap 140 may have a dome shape. In other embodiments the rounded portion may be hemispherical in shape, in other embodiments the rounded portion may be semispherical in shape, and in other embodiments the rounded portion may be in the shape of a geodesic dome. It is understood that the proximal cap 140 may have the same shape as the rounded portion of the distal cap 130, but this is not required. The proximal cap 140 may further include a flat surface 145 that is in direct contact with the grip element 113.

Like the grip element 113, the proximal cap 140 is shaped for complementary joining to the grasping elements 930 of the clamp 900 to facilitate more secure grasping of the intramedullary pin 100. This secure grasping improves the insertion, placement, and extraction of the intramedullary pin 100.

The intramedullary pin 100 may be composed of any materials suitable for insertion into the medullary cavity, such as metals, metal alloys, polymers, ceramic, or combinations thereof.

Figure 2:
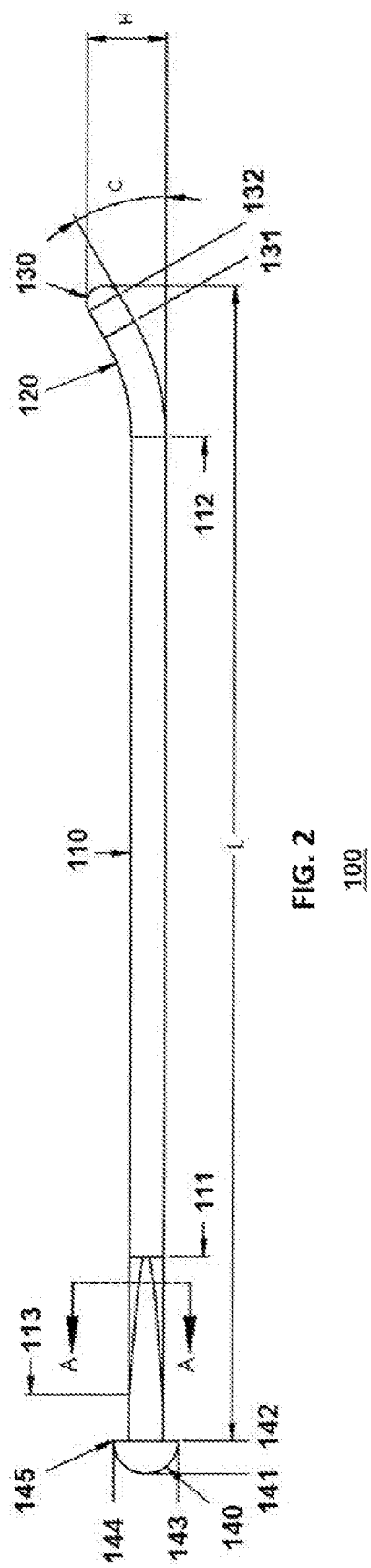
FIG. 2 is a lengthwise profile view of the intramedullary pin embodiment depicted in FIG. 1.

FIG. 2 shows a cross-sectional view of the intramedullary pin 100 depicted in FIG. 1, with exemplary dimensional details. As in FIG. 1, the intramedullary pin 100 shown in FIG. 2 may comprise a main body 110, proximal boundary 111, distal boundary 112, curved extension 120, distal cap 130, intermediate boundaries 131 and 132, proximal cap 140, and flat surface 145.

As shown in FIG. 2, the intramedullary pin 100 has a length L extending from the flat surface 145 of the proximal cap 140 to the end 131 of the distal cap 130. In some embodiments, the length L may be between about 10 mm and about 100 mm. In other embodiments, the length L may be between about 30 mm and about 80 mm, and in other embodiments the length L may be between about 40 mm and 70 mm. In a more particular embodiment, the length L may be 50 mm. The diameter of the main body 110 may be between about 1 mm and 5 mm, in some embodiments. In other embodiments, the diameter of the main body 110 may be between about 2 mm and 4 mm, and in other embodiments, the diameter of the main body 110 may be between 1 mm and 2 mm. In a more particular embodiment, the diameter of the main body 110 may be about 1.6 mm.

In some embodiments, the curved extension 120 and the distal cap 130 have a combined length of between about 5 mm and about 10 mm, when measured in the horizontal direction. In other embodiments, the combined length of these elements is between about 6 mm and about 8 mm. In a more particular embodiment, the combined length of the curved extension 120 and the distal cap 130 is about 7.1 mm. Within the distal cap 130, some embodiments of the cylindrical portion between intermediate boundaries 131 and 132 have a length of about 0.5 mm to about 5 mm, when measured along the main axis of the distal cap itself. In other embodiments, the cylindrical portion have a length of about 1 mm to 3 mm, and in other embodiments, the cylindrical portion have a length of about 1 mm to about 2 mm. In a more particular embodiment, the cylindrical portion may have a length of about 1.44 mm.

The curved extension 120 may have a degree of curvature C directed away from the main axis of the intramedullary pin 100, as shown in FIG. 2. In some embodiments the degree of curvature C is between about 1° and about 45°. In some embodiments, the degree of curvature C may be between about 5° and about 45°. In some embodiments, the degree of curvature C may be between about 10° and about 40°. In some embodiments, the degree of curvature C may be between about 15° and about 35°. In some embodiments, the degree of curvature C may be about 20° and about 30°. In some embodiments, the degree of curvature C may be about 25° and about 35°. In some embodiments, the degree of curvature C is about 25°. In some embodiments, the degree of curvature C is about 30°.

The curved extension 120 and the distal cap 130 may contribute to the height H of the intramedullary pin 100 as shown in FIG. 2. In some embodiments, the height H of the Intramedullary pin is between about 0.5 mm and 10 mm, in other embodiments, the height H is between about 2 mm and 7 mm, and in other embodiments, the height H is between about 3 mm and 5 mm. In a more particular embodiment, the height H is about 3.7 mm.

The dimensions of the proximal cap 140 may be defined with reference to lengthwise endpoints 141 and 142 and height-wise endpoints 143 and 144, as shown in FIG. 2. In some embodiments, the distance between the lengthwise endpoints 141 and 142 is between about 0.5 mm and about 4 mm, and in other embodiments the distance between lengthwise endpoints 141 and 142 is between about 1 mm and about 3 mm, and in other embodiments, the distance between lengthwise endpoints 141 and 142 may be between 1 mm and 2 mm. In a more particular embodiment, the distance between lengthwise endpoints 141 and 142 may be between 1.37 mm and 1.50 mm. In another particular embodiment, the distance between lengthwise endpoints 141 and 142 may be about 1.37 mm, and in a further particular embodiment, the distance between lengthwise endpoints 141 and 142 may be about 1.50 mm.

As shown in FIG. 2, the proximal cap 140 may also include height-wise endpoints 143 and 144. In some embodiments, the distance between height-wise endpoints 143 and 144 is between about 0.5 mm and about 5 mm, in other embodiments the distance between height-wise endpoints 143 and 144 is between about 1 mm and about 4 mm, and in other embodiments the distance between height-wise endpoints 143 and 144 is between about 2 mm and about 3 mm. In a more particular embodiment, the distance between height-wise endpoints 143 and 144 is between about 2.87 mm, and in a further particular embodiment, the distance between height-wise endpoints 143 and 144 is between about 3.00 mm.

It is understood that the distance between height-wise endpoints 143 and 144 may be the spherical diameter of the proximal cap 140. It is further understood that the distance between height-wise endpoints 143 and 144 and the height H of the Intramedullary pin may be the same, but this is not required.

As shown in FIG. 2, the flat surface 145 of the proximal cap 140 may be in direct contact with the grip element 113 of the main body 110, and the grip element 113 may be contoured to facilitate secure grasping by the clamp 900, as described above. In some embodiments, the distance between the flat surface 145 and the contours of the grip element 113 is between about 0.5 mm and about 5 mm, in some embodiments the is between about 1 mm and about 3 mm, and in some embodiments the distance between the flat surface 145 and the contours of the grip element 113 is between about 1 mm and about 2 mm. In a more particular embodiment, the distance between the flat surface 145 and the contours of the grip element 113 is about 1.78 mm.

FIG. 3 shows a cross-sectional view of the exemplary intramedullary pin 100 depicted in FIGS. 1 and 2 at the bisecting line A-A within the grip element 113 in FIG. 2. FIG. 3 shows the width and height of the grip element 113, as defined by widthwise endpoints 310 and 320 and height-wise endpoints 330 and 340.

In some embodiments, the distance between the widthwise endpoints 310 and 320 is between about 0.5 mm and about 5 mm, in other embodiments the distance between the widthwise endpoints 310 and 320 is between about 1 mm and about 3 mm, and in other embodiments the distance between the widthwise endpoints 310 and 320 is between about 1 mm and about 2 mm. In a more particular embodiment, the distance between the widthwise endpoints 310 and 320 is about 1.57 mm.

In some embodiments, the distance between the height-wise endpoints 330 and 340 is between about 0.5 mm and about 5 mm; in other embodiments, the distance between the height-wise endpoints 330 and 340 is between about 1 mm and about 3 mm; and in other embodiments the distance between the height-wise endpoints 330 and 340 is between about 1 mm and about 2 mm. In a more particular embodiment, the distance between the height-wise endpoints 330 and 340 is about 1.57 mm.

It is understood that the distance between the widthwise endpoints 310 and 320 and the height-wise endpoints 330 and 340 may be the same, such that the grip element 113, and/or the main body 110, may have a symmetrical cross-section; however, this is not required. FIGS. 4 to 8 show perspective views of embodiments of the intramedullary pin 100 having varying lengths, as measured horizontally from the end the proximal cap to the end of the distal cap. In the embodiment shown in FIG. 4, the intramedullary pin 100 have a horizontal length of about 50 mm. In the embodiment shown in FIG. 5, the intramedullary pin 100 have a horizontal length of about 55 mm. In the embodiment shown in FIG. 6, the intramedullary pin 100 has a horizontal length of about 60 mm. In the embodiment shown in FIG. 7, the intramedullary pin 100 has a horizontal length of about 65 mm. In the embodiment shown in FIG. 8, the intramedullary pin 100 has a horizontal length of about 70 mm. In an additional embodiment, not depicted in FIGS. 4 to 8, the intramedullary pin 100 has a horizontal length of 40 mm. In a further embodiment, the intramedullary pin 100 has a horizontal length of 45 mm.

Clamp

Another aspect of the present application relates to a clamp for holding an item. The item may be any item that can be grasped or held by the clamp. In some embodiments, the clamp comprises a handle; two blades; a pivot; and one or more grasping elements including a notch, at least one protrusion, and a groove, where at least one of the grasping elements has at least one contour. The clamp can be used for holding or grasping any suitable items, including but are not limited to, medical and surgical devices such as intramedullary nails, bone pins, intramedullary pins, wires, K-wires, surgical wires, fasteners, and needles. The clamp may also be used to hold or grasp tissues and blood vessels.

In some embodiments, the clamp is designed for grasping an intramedullary pin, In some embodiments, the at least one contour on the at least one grasping elements comprises at least one of an angled surface, depression, hatching, indentation, protuberance, ridge, slot, rail, track, hook, loop, alternating smooth and course section, or a combination thereof.

In other embodiments, the at least one contour on the at least one grasping element is structurally complementary to the contour on a grip element of the intramedullary pin.

In other embodiments, the notch of the clamp has an inverse hemispherical shape that fits into a proximal cap of the intramedullary pin.

In other embodiments, the clamp is designed to grasp the intramedullary pin of the present application.

In other embodiments, at least one of the handle, blades, pivot, and grasping elements of the clamp is composed of at least one of stainless steel, titanium and nitinol.

Figure 9:
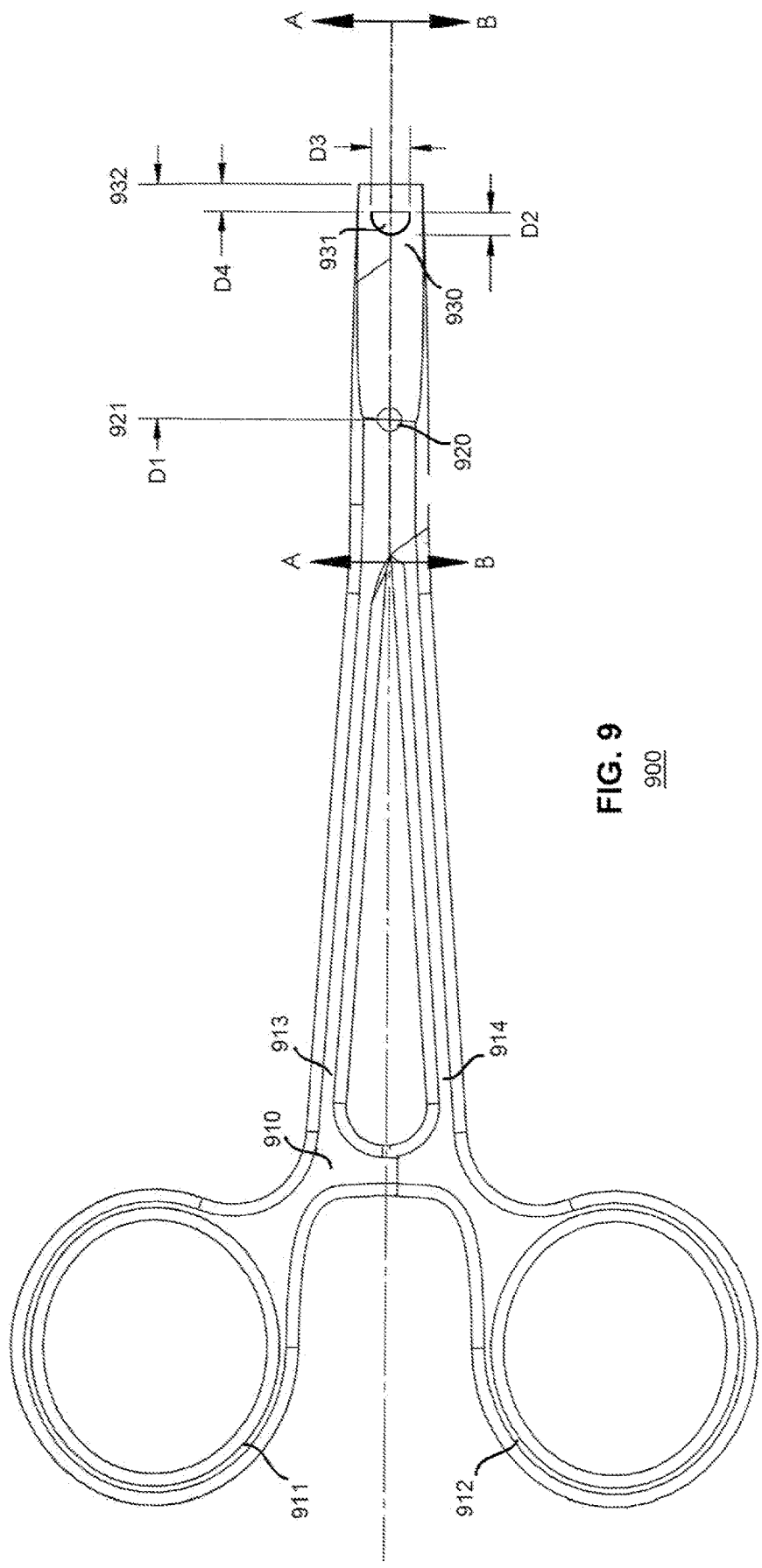
FIG. 9 is a perspective view of an embodiment of a clamp of the present application.

FIG. 9 shows an exemplary clamp 900 of the present application in a fully closed position. The clamp 900 comprises a handle 910, pivot 920, and grasping elements 930.

The handle 910 is located at the proximal end of the clamp 900 and may further include finger holds 911 and 912 to facilitate holding and operation by a medical practitioner. Blades 913 and 914 extend in the distal direction from the finger holds 911 and 912, and may constitute the majority of the length of the clamp 900. The extension of the blades 913 and 914 in a lengthwise direction forms the main axis of the clamp 900.

In some embodiments, the blades 913 and 914 are separated at the proximal end of the clamp 900 to support the finger holds 911 and 912, and the blades 913 and 914 converge to an interlocking position at the distal end, and the pivot 920 is located at this convergence. The pivot 920 may rotate around a pivot center point 921 and this rotation may result in movement of the blades 913 and 914 away from the main axis of the clamp 900.

The grasping elements 930 are located at the distal end of the clamp 900 and include indented notches 931. In some embodiments, the grasping elements 930 further include a blade tip 932, formed by the ends of the blades 913 and 914.

The grasping elements 930 are operated to clasp the grip element 113 of the intramedullary pin 100. As previously noted, in some embodiments the proximal cap 140 has a dome, hemispherical, or semispherical shape, and embodiments of the grasping elements 930 may include a complementarily-shaped notch 931. For example, an embodiment of the intramedullary pin 100 having a hemispherical shape proximal cap 140 may be paired with a clamp 900 having a correspondingly inverse hemispherical notch 931.

This complementary relationship between the notch 931 and the proximal cap 140 allows the clamp 900 to securely grasp the intramedullary pin 100. A medical practitioner may employ the clamp 900 to insert and place the intramedullary pin 100 within the intramedullary cavity to immobilize a reduced bone fracture. Aligning the notch 931 and proximal cap 140 allows the practitioner to perform this operation with improved control over the intramedullary pin 100. This improved control reduces the risk of dislocating the bone fragments during the insertion and placement of the intramedullary pin 100, and reduces the disruption to the bone or the surrounding tissue caused by this process. Should the need arise to remove the intramedullary pin 100, the grasping and extraction process will be similarly improved.

In other embodiments, the grasping elements 930 may be contoured or shaped in a complementary way to these elements of the intramedullary pin 100 that is not strictly inverse. In such embodiments, the clamp 900 may be used with a variety of embodiments of pins, which may allow the economical use of fewer clamps for a larger range of pins.

With reference to FIG. 9, exemplary dimensions of the clamp 900 will be described. In some embodiments, the distance between the pivot center point 921 and the blade tip 932 (shown as D1 in FIG. 9) is between about 0.25 inch and about 2 mm, and in other embodiments the distance D1 is between about 0.5 inch and about 1 inch. In a more particular embodiment, the distance D1 is about 0.75 inch.

The notch 931 may include proximal edge points and distal edge points. In some embodiments, the distance between a proximal edge point and a distal edge point of the notch 931 (shown as D2 in FIG. 9) is between about 0.025 inch and about 0.125 inch, and in other embodiments the distance D2 is between about 0.05 inch and about 0.1 inch. In a more particular embodiment, the distance D2 is about 0.075 inch, and in a further particular embodiment, the distance D2 is about 0.08 inch. The distance D2 is understood as the length of the notch 931.

In some embodiments, the distance between two distal edge points at the distal corners of the notch 931 (shown as D3 in FIG. 9) is between about 0.02 inch and about 0.2 inch. In other embodiments, the distance D3 is between about 0.05 inch and about 0.18 inch, and in other embodiments, the distance D3 is between about 0.08 inch and about 0.16 inch. In a more particular embodiment, the distance D3 is about 0.124 inch, and in a further particular embodiment the distance D3 is about 0.13 inch. The distance D3 may be understood as the height of the notch 931.

Under the foregoing dimensions, the notch 931 may be symmetrical about the main axis, including the bisecting lines A-A and B-B shown in FIG. 9. However, it is to be understood that this symmetry is not required, particularly if the corresponding shape of the proximal cap 140 is not symmetrical.

In some embodiments, the distance between a distal edge point of the notch 931 and the blade tip 932 (shown as D4 in FIG. 9) is between about 0.01 inch and about 0.2 inch. In other embodiments, the distance D4 is between about 0.05 inch and about 0.15 inch, and in other embodiments, the distance D4 is between about 0.08 inch and about 0.1 inch. In a more particular embodiment, the distance D4 is about 0.09 inch.

Figure 10:
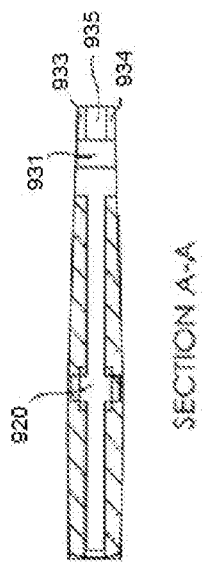
FIG. 10 is an excerpted lengthwise cross-sectional view of the clamp embodiment depicted in FIG. 9.
Figure 11:
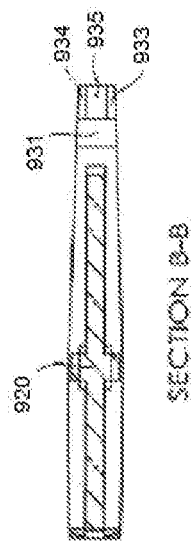
FIG. 11 is an excerpted lengthwise cross-sectional view of the clamp embodiment depicted in FIG. 9.

FIG. 10 is an excerpted cross-sectional view of the clamp 900 at the A-A bisecting line depicted in FIG. 9, and FIG. 11 is an excerpted cross-sectional view of the clamp 900 at the B-B bisecting line depicted in FIG. 9, with inverse cross-hatching for perspective. With reference to both FIG. 10 and FIG. 11, the clamp 900 may include the pivot 920 and grasping elements 930 having notch 931.

The grasping elements 930 may further include protrusions 933 and 934 and a groove 935. These additional grasping elements may operate to grasp the grip element 113 of the main body 110. As previous noted, the grip element 113 may be contoured along its length, and that the contours corresponds to the protrusions 933 and 934 and a groove 935 grasping elements. For example, the grip element 113 may have contours in the shape of angled surfaces, and the protrusions 933 and 934 and a groove 935 may have complementary, inverse angled surfaces to facilitate a secure grasp of the grip element 113 by the grasping elements 930. Like the notch 931 and the proximal cap 140, this complementary relationship provides a medical practitioner with improved control over the intramedullary pin 100 when using the clamp 900, which may reduce the risk of dislocation and disruption during the insertion, placement, and extraction of the intramedullary pin 100.

The cross-sections of the notch 931, protrusions 933 and 934, and groove 935 shown in FIGS. 10 and 11 may be symmetrical across the A-A and B-B bisecting lines, respectively. It is understood, however, that this symmetry is not required, particularly if the grip element 113 and the proximal cap 140 are not symmetrical.

Figure 13A:
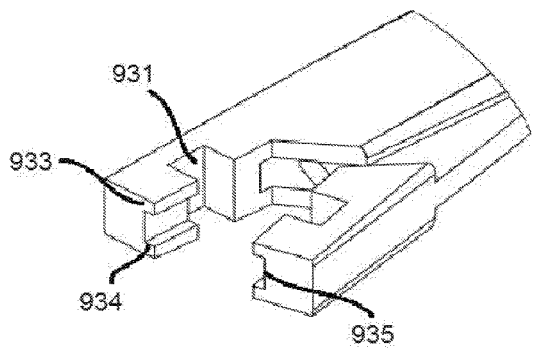
FIG. 13A is an excerpted perspective view of the grasping elements of the clamp embodiment depicted in FIG. 12.
Figure 13B:
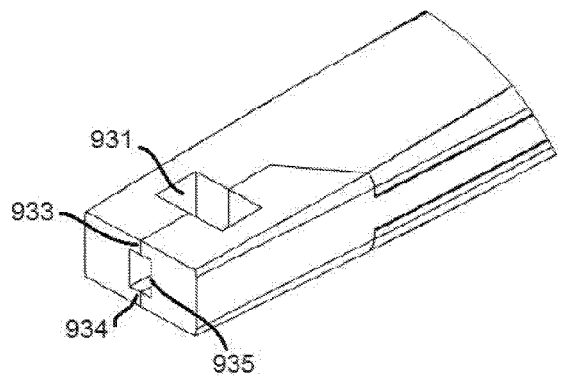
FIG. 13B is an excerpted perspective view of the grasping elements of the clamp embodiment depicted in FIG. 12.

FIG. 12 shows a perspective view of the clamp 900 depicted in FIG. 9 in an open position. FIGS. 13A and 13B show an excerpted view of the grasping elements 930 depicted in FIG. 12 within section D. In FIGS. 12, 13A, and 13B, the interior surfaces of the grasping elements 30 are visible, including the notch 931, protrusions 933 and 934, and the groove 935. These interiors of the notch 931, protrusions 933 and 934, and the groove 935 are shown in these figures as planar and without contours, marking, or shaping. However, it is understood that such features may be present if found on the grip element 113 and proximal cap 140 of the intramedullary pin 100.

FIG. 13A shows the grasping elements 930 when the clamp 900 is in the open position, and FIG. 13B shows these elements when the clamp 900 is in the closed position. The embodiment of FIG. 13B depicts the alignment of the protrusions 933 and 934 to form the groove 935. It is understood that this alignment may occur regardless of the contours, marking, or shaping applied to the protrusions 933 and 934.

Figure 13C:
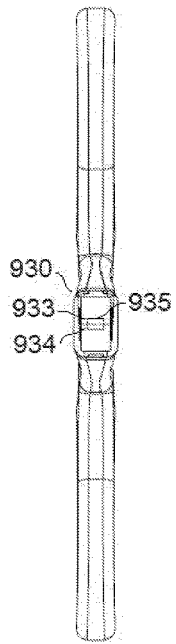
FIG. 13C is a widthwise cross-sectional view of the grasping elements of the clamp embodiment depicted in FIG. 12.
Figure 13D:
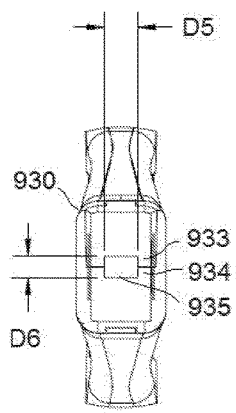
FIG. 13D is an excerpted widthwise cross-sectional view of the grasping elements of the clamp embodiment depicted in FIG. 9.

FIG. 13C shows a widthwise cross-sectional view from the distal end of the exemplary clamp 900 depicted in FIG. 9, and FIG. 13D shows an excerpted widthwise cross-sectional view from the distal end of the exemplary clamp 900 depicted in FIG. 9. The clamp 900 is in the fully closed position in FIGS. 13C and 13D. The gasping elements 930 and the blade tip 932 are visible in FIGS. 13C and 13D, along with the protrusions 933 and 934 and the groove 935.

In some embodiments, the distance between the edges of the protrusions 933 and 934 forming the groove 935 in the horizontal direction from the perspective of FIG. 13D (shown as D5 in FIG. 13D) is between about 0.01 inch and about 1 inch. In other embodiments, the distance D5 is between about 0.02 inch and 0.08 inch. In a more particular embodiment, the distance D5 is about 0.7 inches.

FIG. 13D depicts the distance between the edges of the groove 935 formed by the protrusions 933 and 934 in the heightwise direction from the perspective of FIG. 13D (shown as D6 in FIG. 13D). In some embodiments, the distance D6 is between about 0.02 inches and about 0.06 inches, and in other embodiments, the distance D6 is between about 0.03 inches and about 0.05 inches. In a more particular embodiment, the distance D6 is about 0.04 inches.

The distances D5 and D6 are depicted in FIGS. 13C and 13D as symmetrical about the groove 935 and evenly spread between protrusion 933 and protrusion 934. However, it is understood that such symmetry and even distribution is not required, and instead the distances D5 and D6 may be asymmetrical or otherwise non-uniform, especially if the corresponding shape of the proximal cap 140 is not symmetrical.

Instrument Kit

Another aspect of the present application relates to an instrument kit. In some embodiments, the instrument kit contains one or more pins of the present application. In some embodiments, the kit is a kit for immobilizing a reduced bone fracture and includes one or more intramedullary pins of the present application. In some embodiments, the intramedullary pin includes a main body having a proximal boundary and a distal boundary; a curved extension having a degree of curvature of at least 1°, where the curved extension is in direct contact with the distal boundary; a distal cap having a cylindrical portion and a rounded portion, where the cylindrical portion is in direct contact with the curved extension; a grip element having at least one contour, where the grip element is in direct contact with the proximal boundary; and a proximal cap having a flat surface, where the proximal cap is in direct contact with the grip element. In some embodiments, a distal boundary of the main body is in direct contact with the curved extension, the curved extension is in direct contact with the cylindrical portion of the distal cap, a proximal boundary of the main body is in direct contact with the grip element, and the grip element is in direct contact with the flat surface of the proximal cap.

In other embodiments, the at least one contour of the grip element of the intramedullary pin of the present application comprises at least one of an angled surface, depression, hatching, indentation, protuberance, ridge, slot, rail, track, hook, loop, alternating smooth and coarse section, or a combination thereof. In other embodiments, the at least one contour of the grip element is structurally complementary to at least one contour on a grasping element of a clamp. In other embodiments, the proximal cap has a hemispherical shape that fits into a notch in a clamp. In other embodiments, the main body, the curved extension, the distal cap, the grip element, and the proximal cap are composed of at least one of stainless steel, titanium, nitinol, and a bioabsorbable material. In some embodiments, the curved extension has a degree of curvature in the range of about 1° to 45°, 5° to 45°, 10° to 40°, 20° to 30° or 25° to 35°. In some embodiments, the curved extension has a degree of curvature of about 25° or about 30°.

In some embodiments, the instrument kit further includes a clamp of the present application. In some embodiments, the clamp comprises a handle; two blades; a pivot; and one or more grasping elements including a notch, at least one protrusion, and a groove, wherein at least one of the grasping elements has at least one contour. In some embodiments, the clamp is designed for grasping an intramedullary pin. In some embodiments, the clamp is designed for grasping the intramedullary pin of the present application.

In some embodiments, the at least one contour on the at least one grasping elements of the clamp comprises at least one of an angled surface, depression, hatching, indentation, protuberance, ridge, slot, rail, track, hook, loop, alternating smooth and course section, or a combination thereof. In other embodiments, the at least one contour on the at least one grasping element is structurally complementary to the contour on a grip element of the intramedullary pin. In other embodiments, the notch of the clamp has an inverse hemispherical shape that fits into a proximal cap of the intramedullary pin. In other embodiments, the handle, blades, pivot, and grasping elements are composed of at least one of stainless steel, titanium and nitinol.

In some embodiments, the instrument kit of the present application includes a clamp of the present application. In some embodiments, the clamp comprises a handle; two blades; a pivot; and one or more grasping elements including a notch, at least one protrusion, and a groove, wherein at least one of the grasping elements has at least one contour. In some embodiments, the clamp is designed for grasping an intramedullary pin. In some embodiments, the clamp is designed for grasping the intramedullary pin of the present application. In some embodiments, the at least one contour on the at least one grasping elements of the clamp comprises at least one of an angled surface, depression, hatching, indentation, protuberance, ridge, slot, rail, track, hook, loop, alternating smooth and course section, or a combination thereof. In other embodiments, the at least one contour on the at least one grasping element is structurally complementary to the contour on a grip element of the intramedullary pin. In other embodiments, the notch of the clamp has an inverse hemispherical shape that fits into a proximal cap of the intramedullary pin. In other embodiments, at least one of the handle, blades, pivot, and grasping elements of the clamp is composed of at least one of stainless steel, titanium and nitinol.

In some embodiment, the instrument kit of the present application is a surgical instrument kit that includes an intramedullary pin and a clamp, where the intramedullary pin includes a main body having a proximal boundary and a distal boundary; a curved extension having a degree of curvature of at least 1°, where the curved extension is in direct contact with the distal boundary; a distal cap having a cylindrical portion and a rounded portion, where the cylindrical portion is in direct contact with the curved extension; a grip element having at least one contour, where the grip element is in direct contact with the proximal boundary; and a proximal cap having a flat surface, where the proximal cap is in direct contact with the grip element. In one embodiment, the clamp includes a handle; two blades; a pivot; and grasping elements including a notch, at least one protrusion, and a groove, where at least one of the grasping elements has at least one contour In some embodiments, the kit further includes an awl for puncturing a hole in the bone to allow for the passage of the intramedullary pin.

Method for Immobilizing a Reduced Bone Fracture

Another aspect of the present application relates to a method of immobilizing a reduced bone fracture using the intramedullary pin of the present application. In some embodiments, the method comprises the steps of establishing an access point to the medullary cavity of a fractured bone in a subject, reducing the bone fragments at the fracture, aligning the intramedullary pin at replace access point, and inserting the intramedullary pin at replace access point and into the intramedullary cavity, thereby reducing the movement of, or immobilizing, the bone fragments in the reduced state. In some embodiments, the access point is a hole in the bone. In other embodiments, the hole is created with a drill, and in other embodiments, the hole is created with an awl. In some embodiments, the fractured bone is a long bone. In other embodiments, the long bone is selected from the group consisting of metatarsal bones and metacarpal bones, wherein the metatarsal bones and metacarpal bones include the phalanges. In some embodiments, the subject is a mammal. In some embodiments, the subject is a human. In some embodiments, the subject is a pet. In some embodiments, the subject is an animal.

Another aspect of the present application relates to a method of immobilizing a reduced bone fracture using the intramedullary pin and clamp of the present application. In some embodiments, the method comprises the steps of establishing an access point to the medullary cavity of the bone, reducing the bone fragments at the fracture, grasping a grip element and a proximal cap the intramedullary pin with one or more grasping elements of the clamp, aligning the intramedullary pin at replace access point, and inserting the intramedullary pin at replace access point and into the intramedullary cavity, thereby reducing the movement of, or immobilizing, the bone fragments in the reduced state. In some embodiments, the subject is a mammal. In some embodiments, the subject is a human. In some embodiments, the subject is a pet. In some embodiments, the subject is an animal. In some embodiments, the access point is a hole in the bone. In other embodiments, the hole is created with a drill, and in other embodiments, the hole is created with an awl. In some embodiments, the fractured bone is a long bone. In other embodiments, the long bone is selected from the group consisting of metatarsal bones and metacarpal bones, wherein the metatarsal bones and metacarpal bones include the phalanges.

EXAMPLE 1

Reduction and Immobilization of Fractured Metacarpal Bone

A subject presents with a fracture near the distal end of the second metacarpal bone on the left hand. The hand is x-rayed and the nature of the fracture indicates implantation of an intramedullary pin as the desired therapeutic approach.

The metacarpophalangeal joint is flexed 90 degrees exposing the metacarpal head, allowing direct access by the intramedullary pin. The fracture is reduced and held in place and a medical practitioner grasps the proximal cap and grip elements of the intramedullary pin with the grasping elements of the clamp. Using the clamp, the practitioner inserts the distal cap, curved extension, and main body of the intramedullary pin into the medullary canal of the phalanx, immobilizing the reduced fragments of the metacarpal in the correct position to allow union of the fragments at the fracture. The practitioner releases the clamp's grasp on the grip elements and proximal cap of the intramedullary pin, and removes the clamp from the insertion site. In some embodiments, the practitioner may tap the top of the proximal cap so that it is flush with the bone.

The above description is for the purpose of teaching the person of ordinary skill in the art how to practice the present invention, and it is not intended to detail all those obvious modifications and variations of it which will become apparent to the skilled worker upon reading the description. In addition, the drawings are merely illustrative and may not be drawn to scale. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A clamp for grasping an intramedullary pin, comprising:
    a handle at a proximal end of the clamp;
    two blades extending from the handle;
    a pivot adjacent the blades and a distal end of the clamp; and
    a plurality of grasping elements extending from the blades, the plurality of grasping elements comprising at least one notch, at least one protrusion, and at least one groove,
    wherein at least one grasping element comprises a contour; and
    wherein the at least one notch has a concave hemispherical proximal side and a flat distal side situated opposite the concave hemispherical proximal side, the concave hemispherical proximal side and the flat distal side together defining an inverse hemispherical shape that is structurally complementary to a proximal cap of the intramedullary pin.

2. The clamp of claim 1, wherein the contour comprises an angled surface, depression, hatching, indentation, protuberance, ridge, slotted section, tracking section, hook, loop, alternating smooth and coarse section, or a combination thereof.

3. The clamp of claim 1, wherein the contour on the grasping element is structurally complementary to a contour on a grip element of the intramedullary pin.

4. The clamp of claim 1, wherein at least one of the handle, blades, pivot, and grasping elements is composed of at least one of stainless steel, titanium and nitinol.

5. The clamp of claim 4, wherein the handle, blades, pivot, and grasping elements are composed of at least one of stainless steel, titanium and nitinol.

6. The clamp of claim 5, wherein the handle, blades, pivot, and grasping elements are composed of stainless steel.

7. An instrument kit, comprising the clamp of claim 1 and one or more intramedullary pin.

8. The instrument kit of claim 7, further comprising an awl for puncturing a hole in a bone to allow for the passage of the intramedullary pin.

* * * * *